(12) United States Patent
Hensley et al.

(10) Patent No.: US 9,451,904 B2
(45) Date of Patent: Sep. 27, 2016

(54) METHOD AND APPARATUS FOR ENDOSCOPIC EXAMINATION OF LESIONS

(75) Inventors: Harvey Hensley, Newtown Square, PA (US); Margie Clapper, Harleysville, PA (US)

(73) Assignee: FOX CHASE CANCER CENTER, Jenkintown, PA (US)

( * ) Notice: Subject to any disclaimer, the term of this patent is extended or adjusted under 35 U.S.C. 154(b) by 586 days.

(21) Appl. No.: 12/579,529

(22) Filed: Oct. 15, 2009

(65) Prior Publication Data

US 2010/0092054 A1 Apr. 15, 2010

Related U.S. Application Data

(63) Continuation of application No. 12/595,967, filed as application No. PCT/US2008/060618 on Apr. 17, 2008.

(60) Provisional application No. 60/912,426, filed on Apr. 17, 2007, provisional application No. 60/912,584, filed on Apr. 18, 2007.

(51) Int. Cl.
*G06T 7/00* (2006.01)
*A61B 5/107* (2006.01)
*A61B 5/00* (2006.01)
(Continued)

(52) U.S. Cl.
CPC ......... *A61B 5/1076* (2013.01); *A61B 1/00087* (2013.01); *A61B 1/00147* (2013.01); *A61B 5/704* (2013.01); *G06T 7/0012* (2013.01); *A61B 1/31* (2013.01); *A61B 2503/40* (2013.01)

(58) Field of Classification Search
CPC .............. A61B 5/0084; A61B 5/6852; A61B 2017/2924; A61B 19/26; A61B 19/22; A61B 1/00193; H04N 2005/2255; G02B 23/2415; G06T 7/0012; G06T 2207/10068
USPC .......... 382/128; 600/109–111, 117, 127, 129
See application file for complete search history.

(56) References Cited

U.S. PATENT DOCUMENTS 4,980,763 A * 12/1990 Lia .................................. 348/67
5,412,823 A * 5/1995 Sitta ..................... A61B 6/0457
378/209

(Continued)

OTHER PUBLICATIONS

Pooley et al., Imaging & Therapeutic Technolgy: The AAPM/RSNA Physics Tutorial for Residents: Digital Fluoroscopy. RadioGraphics 2001 [on-line], Mar.-Apr. 2001 [retrieved on Mar. 7, 2013], vol. 21, No. 2, pp. 521-534. Retrieved from the Internet: http://radiographics.rsna.org/content/21/2/521/short.*

(Continued)

*Primary Examiner* — Matthew Bella
*Assistant Examiner* — Dennis Rosario
(74) *Attorney, Agent, or Firm* — Stephen H. Eland; Dann, Dorfman, Herrell & Skillman (57) ABSTRACT

An apparatus is provided, which utilizes an adjustment platform for supporting a subject during the endoscopic examination. Additionally, a method for performing an endoscopic examination is also provided in which an endoscope is inserted into a subject and the endoscope is maintained at a generally fixed position while the position of the subject is adjusted to advance the endoscope into the subject. Further still, a method is provided for estimating the size of sample tissue using an endoscope and a reference element. Based on known parameters of the reference element, the size of the area being examined can be estimated.

7 Claims, 4 Drawing Sheets

(51) Int. Cl.
*A61B 1/00* (2006.01)
*A61B 1/31* (2006.01)

(56) References Cited

U.S. PATENT DOCUMENTS

| | | | |
|---|---|---|---|
| 5,781,943 A * | 7/1998 | Moenning et al. | 5/81.1 C |
| 6,084,941 A | 7/2000 | Stenstrom | |
| 6,131,214 A * | 10/2000 | Moenning | A61G 7/001 |
| | | | 193/35 F |
| 6,400,980 B1 | 6/2002 | Lermeison | |
| 6,459,481 B1 * | 10/2002 | Schaack | 356/241.1 |
| 6,471,637 B1 * | 10/2002 | Green | A61B 1/00045 |
| | | | 600/109 |
| 7,551,955 B2 * | 6/2009 | Adler | 600/424 |
| 7,634,305 B2 * | 12/2009 | Davidson et al. | 600/424 |
| 2006/0225211 A1 | 10/2006 | Verhoeven | |

OTHER PUBLICATIONS

Cano et al., New Methods for Video-Based Tracking of Lararoscopic Tools, Jul. 10-11, 2006 [retrieved Jul. 6, 2016], Lecture Notes in Computer Science: Biomedical Simulation, vol. 4072, pp. 142-149. Retrieved from the Internet: http://link.springer.com/chapter/10.1007%2F11790273_16.*

* cited by examiner

METHOD AND APPARATUS FOR ENDOSCOPIC EXAMINATION OF LESIONS

PRIORITY CLAIM

This application is a continuation of U.S. patent application Ser. No. 12/595,967, filed Oct. 15, 2009, which is a U.S. National Phase application of International Application No. PCT/US08/60618, filed Apr. 17, 2008 which claims priority to U.S. Provisional Application Nos. 60/912,426 filed Apr. 17, 2007 and 60/912,584 filed Apr. 18, 2007. Each of the foregoing applications is incorporated herein by reference.

FIELD OF THE INVENTION

The present invention relates to the field of endoscopy and particularly to the field of evaluating lesions in mammals using endoscopy.

BACKGROUND OF THE INVENTION

During the course of the research, it is necessary to measure lesions to evaluate the progression of growth of the lesion or lesions in test subjects. When the test subjects are small animals, it becomes quite difficult to measure the lesions, and frequently is done via necropsy. However, it is desirable to develop a system in which the lesion growth can be evaluated while the subject is alive so that the continuing growth of the lesion can be monitored.

SUMMARY OF THE INVENTION

In light of the foregoing, the present invention provides a method and apparatus for the endoscopic examination of lesions of subjects, such as small animals. According to one aspect, the invention provides an endoscope assembly and a positioning system for positioning a subject. The positioning system is configured to support the subject and adjust the subject. In one embodiment, the positioning system is operable to adjust the subject in a plurality of directions and angles relative to the endoscope assembly. A fixture may be provided for maintaining the endoscope at a fixed position while the positioning system varies the orientation of the subject relative to the endoscope assembly.

According to another aspect of the present invention, a method for performing an endoscopic procedure of a subject is provided. According to the method, a positioning device having a platform for supporting an subject is provided. The platform is operable to vary the position of the subject while an endoscope is maintained at a fixed position. To perform the procedure, the endoscope is maintained at a generally fixed position while the position of the platform is varied relative to the endoscope assembly.

In one embodiment, the platform is adjustable in a plurality of directions and angles after the subject is mounted on the platform. The endoscope assembly is maintained at a generally fixed location. The orientation and/or the position of the platform is varied to orient the subject relative to the endoscope, while maintaining the endoscope at a generally fixed location. After orienting the subject relative to the endoscope, the subject is displaced relative to the endoscope to place the endoscope within the animal. After the endoscope is inserted into the subject, the endoscope is advanced adjacent an area to which a procedure is to be performed by displacing the subject on the positioning device while maintaining the endoscope in a generally fixed position.

According to another aspect, a method for estimating the size of an object using an endoscope is provided. According to the method, an endoscope is introduced into a subject so that the endoscope is adjacent tissue to be examined. The endoscope is configured to include an element, such as a standard having a known dimension. The endoscope is introduced into the subject so that the standard is adjacent the item to be examined. Based on known parameters of the standard, the size of the area being examined can be estimated.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Referring now to the figures, wherein like elements are numbered alike throughout, an apparatus for endoscopic examination is designated generally 10. The system includes a positioning device 20 and an endoscope assembly 100. The positioning device 20 includes a support for supporting a subject 5.

In the present embodiment, the positioning device 20 is configured to allow the subject 5 to be re-oriented and re-positioned as necessary to orient the subject relative to the endoscope. The positioning device 20 may have one or more adjustments for adjusting the subject 5. In the present instance, the positioning device includes mechanisms for adjusting the position of the subject along a plurality of directions. Additionally, the positioning device may include mechanisms for rotating the subject around one or move axes.

Figure 1:
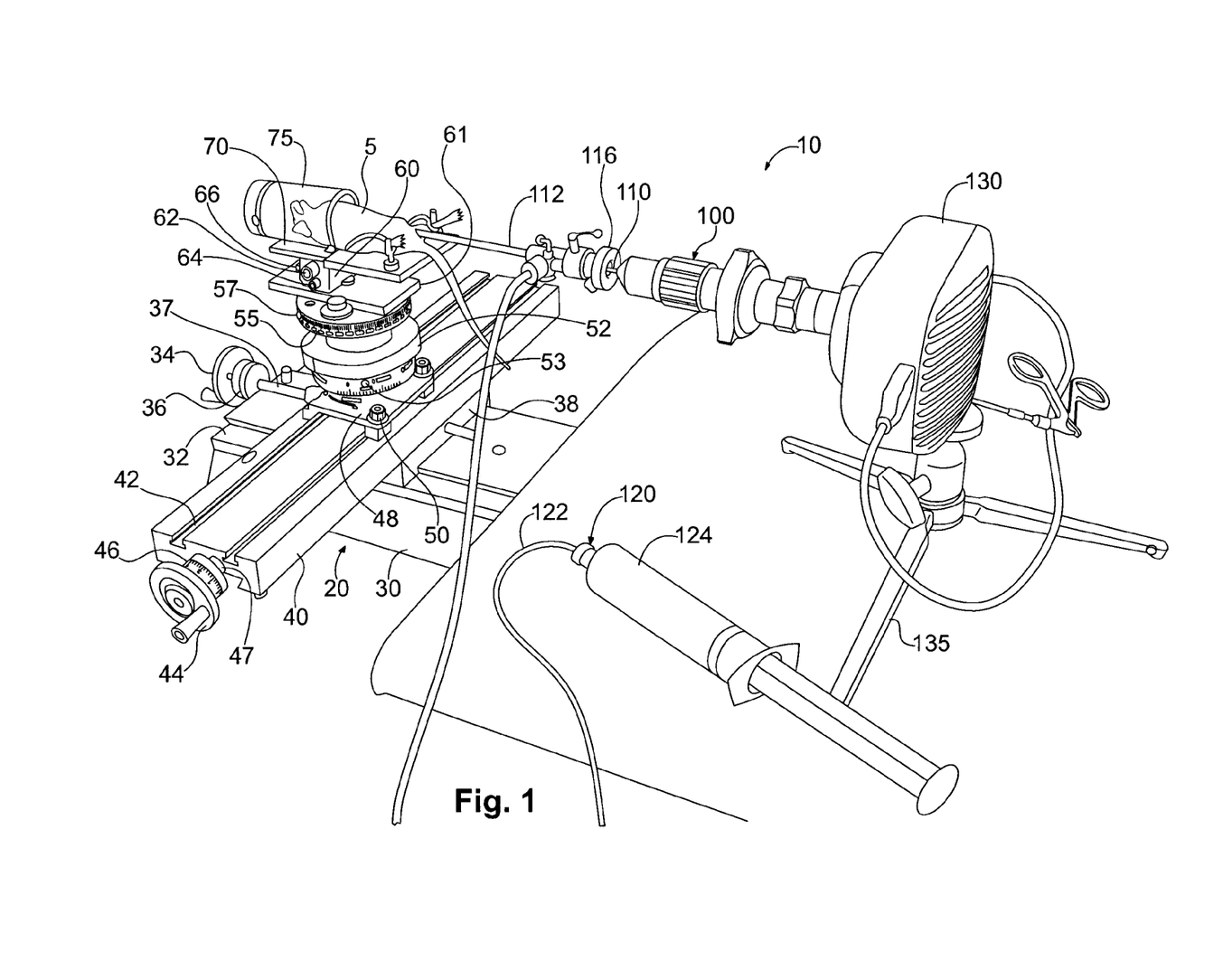
FIG. 1 is a perspective view of an apparatus for the endoscopic examination of a small animal.

In the present instance, the positioning device 20 includes mechanisms for translating the subject along three directions: laterally (identified as the x-direction in FIG. 1), longitudinally (identified as the y-direction in FIG. 1) and vertically (identified as the z-direction in FIG. 1. Additionally, the positioning device may include mechanisms for rotating the subject in three directions: roll (rotation about the x-axis), pitch (rotation about the y-axis), and yaw (rotation about the z-axis). These three translational adjustment mechanisms combined with the three angular adjustment mechanisms, allow the positioning device 20 to precisely position and move the subject relative to the endoscope assembly 100.

Referring to FIG. 1, the mechanisms for translating the subject in three directions will be described in greater detail. The positioning device 20 includes a table 40 mounted on a saddle 38 to provide lateral adjustment of the subject in the y-direction. The saddle 38 in turn is mounted onto a knee 30 to provide lateral adjustment of the subject in the x-direction.

The knee 30 is an elongated element having guideways 32. The saddle 38 in configured to mate with the guideways 32 so that the saddle is displaceable along the guideways. An adjustment wheel or crank 34 is connected to a threaded element, such as a ball screw 37 connected to the knee 30. A mating threaded element, such as a nut, is connected to the saddle 38, and cooperates with the screw 37. Accordingly, rotating the adjustment wheel 34 rotates the screw 37, which in turn displaces the saddle 38 along the guideways 32 of the knee. The result is displacement of the subject in the x-direction.

To maintain the subject at a fixed lateral position, the device may include a locking element, such as lock 36, which impedes rotation of the handle. Alternatively, the lock 36 may be in the form of a removeable connection between the handle 34 and the threaded element 37. In this way, to lock the table to impede translation in the x-direction, the handle is disconnected from the threaded element, so that rotating the handle does not cause displacement of the table.

Similarly, the saddle 38 has guideways that cooperate with the table 40 to guide the displacement of the table in the longitudinal or y-direction. Specifically, a second adjustment wheel or crank 44 is connected to a threaded element, such as a ball screw, which is connected with the table. A mating threaded element, such as a nut, is connected with the saddle 38. Accordingly, rotating the wheel 44 rotates the ball screw 47, which in turn displaces the table 40 relative to the saddle. The result is displacement of the subject in the y-direction. To maintain the subject at a fixed longitudinal position, the device may include a locking element, such as lock 46. The lock 46 is similar to the lock 36 described above in connection with the mechanism for lateral translation.

A platform 48 is attached to the top of the table 40. In the present instance, the table 40 includes a plurality of t-slots 42. The platform 48 is attached to the table using a plurality of t-slot connector that engage the t-slots 42 and project upwardly.

A vertical adjustment mechanism 50 is mounted on the platform 48. The vertical adjustment mechanism 50 comprises a collar 52 that engages a threaded post. Rotating the collar 52 vertically displaces the subject. Additionally, the vertical adjustment mechanism 50 may include a lock 53 to fix the vertical position of the subject. In the present instance, the lock 53 is a set screw that frictionally locks the collar 52 to impede rotation of the collar.

A first angular adjustment mechanism 55 is connected to the top of the vertical adjustment mechanism 50. The first angular adjustment mechanism is operable to rotate the subject 5 about the vertical or z-axis. Accordingly, the first angular adjustment mechanism 55 provides yaw angular adjustment. The yaw adjustment mechanism 55 is essentially a rotatable table. The yaw adjustment mechanism 55 also includes a lock for impeding yaw adjustment of the mechanism. In the present instance, the lock comprises a set screw 57.

Connected to the top of the yaw adjustment mechanism 55 is a second angular adjustment mechanism 60 that allows for angular adjustment of the subject about one or more axes other than the z-axis. For instance, the second adjustment mechanism 60 may be a goniometer that provides displacement of the subject about the x-axis or the y-axis. In the present instance, the second adjustment mechanism 60 is a dual axis goniometer that provides displacement of the subject about both the x-axis and the y-axis. In other words, the goniometer provides roll adjustment (rotation about the x-axis), and pitch adjustment (rotation about the y-axis). A goniometer base 61 connected to the top of the yaw adjustment mechanism 55 connects the goniometer to the yaw adjustment mechanism.

The goniometer 60 includes two adjustment mechanisms for adjusting the pitch and/or roll of the subject. Referring to FIG. 1, a first thumbscrew 62 provides roll adjustment. Specifically, rotating thumbscrew 62 affects rotation of the subject about the x-axis. Similarly, the goniometer includes a second thumbscrew 66 for providing pitch adjustment. The goniometer also includes at least one locking element for preventing angular adjustment of the subject. For instance, the goniometer may include a locking thumbscrew 64 that operates similarly to a set screw to prevent roll adjustment for the subject. Similarly, the goniometer may include a second locking element for preventing pitch adjustment of the subject.

Attached to the top of the goniometer is a platform or table 70 for supporting the subject 5. Additionally, in the present instance a hood is connected to the end of the table 70. The hood may be any of a variety of shapes and sizes configured to accommodate the subject. For instance, in the present instance, the hood is sized to accommodate at least the head, and preferably a portion of the body of the subject 5, such as a mouse. The hood 75 provides a generally enclosed space around the subjects head. As discussed below, anesthesia is introduced into the hood during the procedure to keep the subject anesthetized.

Configured as described above, a subject 5 positioned on the table 70 may be displaced in a vertical, longitudinal or lateral direction by manipulating adjustment wheels 34, 44 or collar 52. Similarly, the roll, pitch and yaw angles of a subject positioned on the table 70 can be adjusted by manipulating thumbscrews 62 and 66 or yaw adjustment element 55. Each of these adjustments can be made in fine increments so that the subject can be precisely translated or rotated.

Endoscope Assembly

Figure 2:
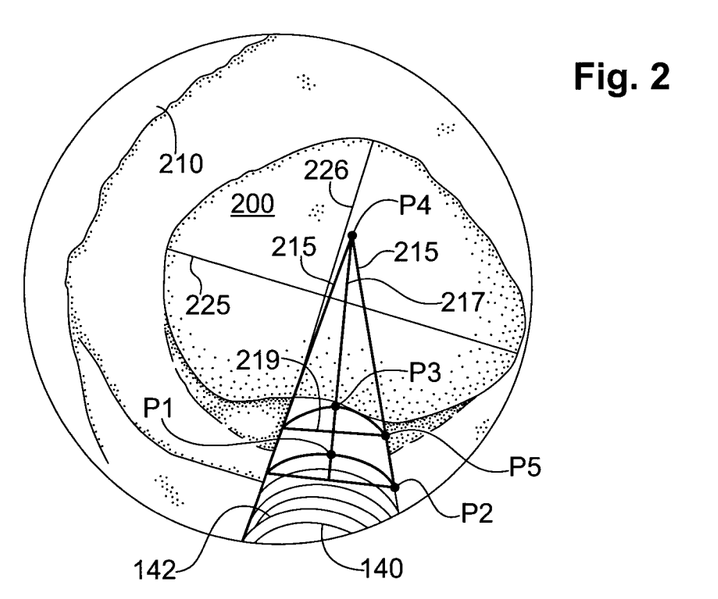
FIG. 2 is an enlarged view of an portion of a subject as viewed from an endoscope assembly.
Figure 3:
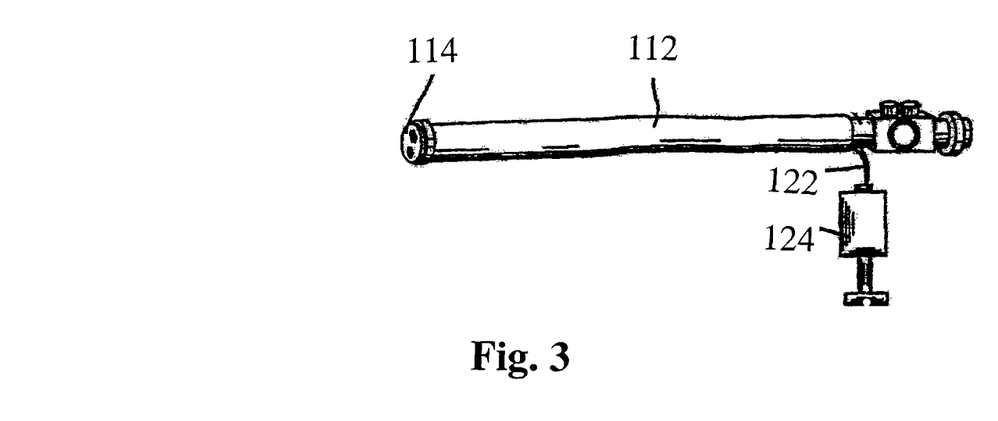
FIG. 3 is a diagrammatic view of an endoscope.

Referring to FIGS. 1-3, the details of the endoscope assembly 100 will now be described in greater detail. The assembly 100 includes an endoscope 110, a sheath 112 surrounding the endoscope and a camera 130 for capturing images from the endoscope.

The endoscope 110 may be any of a variety of commercially available endoscopes. In the present instance, the endoscope is a 1.5 mm diameter endoscope. The sheath 112 is a hollow generally cylindrical element surrounding the endoscope. and has a generally open rearward end. The endoscope 110 extends through the rearward end of the sheath 112, and a seal 116 forms a fluid tight seal at the rearward end of the sheath, between the sheath and the endoscope.

An imaging device 130 is connected to the rearward end of the endoscope. The imaging device may be any of a variety of device for capturing images from the endoscope. In the present instance, the imaging device 130 is a digital camera, such as MicroPublisher 3.3 RTV digital camera.

As shown in FIG. 3, the sheath 112 may have an end cap 114 having one or more apertures. As discussed further below. a scaling rod 140 may extend from one of the apertures to aid in the examination of the subject.

In the present instance, the endoscope assembly also includes a pressure source 120 for sufflating the portion of the patient into which the endoscope is to be introduced. For instance, in the present instance, the endoscope may be introduced transanally into the subject. To sufflate the subject's colon, saline in injected into the subject's colon. Accordingly, the pressure source may include a conduit 122, such as a length of pvc tubing, connected to a syringe 124 containing an quantity of saline. A fluid-tight seal is formed between the tubing and the sheath, so that fluid from the syringe may be injected into the patient, through the sheath.

Referring to FIG. 1, in the present embodiment, the endoscope assembly 100 also includes a stand 135. The stand rigidly supports the camera 130, onto which the endoscope 110 and sheath 112 are mounted. The stand 135 may be configured to adjust the angle or position of the endoscope. However, in the present instance, the stand 135 is configured to maintain the endoscope at a generally fixed position relative to the subject 5, while the positioning system is manipulated to adjust the position and orientation of the subject.

Method of Introducing Endoscope

As described above, the system may be used as follows to perform an endoscopic procedure on a subject. The procedure is particularly suited for performing an endoscopic procedure on small mammals, such as mice, however, the system is not necessarily limited to such use. In the following example, the system is described in connection with a colonoscopy, however, the system may be adapted to a variety of endoscopic procedures.

To begin a procedure, a subject, such as a mouse is placed onto the table 70 on top of the positioning system 20. The subject is anesthetized. One method for doing so is to introduce anesthesia gas into the hood 75, while the subject's head is in the hood. After the subject is anesthetized, the endoscope assembly 100 is placed adjacent the insertion point of the subject. The positioning system 20 is then adjusted to properly position and orient the subject relative to the tip of the endoscope. Specifically, depending on the orientation of the subject relative to the endoscope, the subject may need to be rotated around one or more axes to align the subject at the proper angle relative to the angle of the endoscope. To adjust the yaw angle of the subject relative to the endoscope, the yaw angle mechanism 55 is adjusted as necessary. To adjust the pitch or roll angle of the subject, the goniometer 60 is adjusted as necessary. Similarly, the position of the subject may be adjusted vertically, laterally or longitudinally to align the endoscope with the insertion point of the subject. To adjust the vertical position of the subject, the vertical adjustment collar 52 is rotated. To adjust the longitudinal position of the subject, the first adjustment wheel 34 is rotated, and to adjust the lateral position of the subject, the second adjustment wheel 44 is rotated.

After the subject 5 is properly positioned and aligned with the endoscope, the subject is advanced toward the endoscope 110 to introduce the endoscope into the subject. The subject is advanced by rotating the longitudinal adjustment wheel 34. After the endoscope is introduced into the patient, the patient is sufflated. For instance, saline may be injected into the patient through the endoscope by advancing the plunger in the syringe 124.

As the endoscope advances into the subject, it may be necessary to periodically and incrementally adjust the position or orientation of the subject in order to maintain the endoscope in a proper orientation in the subject. For instance, in the example of a colonoscopy, as the endoscope advances into the subject, the yaw angle may need to be adjusted based on the configuration of the subjects colon. To do so, the yaw angle adjustment mechanism 55 is rotated and the subject is then advanced further toward the endoscope. In this way, the position and orientation of the patient relative to the endoscope can be iteratively adjusted as the endoscope is advanced into the patient. As an adjustment is made, the positioning system 20 can maintain the other variables constant. In other words, while the yaw angle is being adjusted, the positioning system 20 maintains the pitch and roll angle of the patient, as well as the vertical and lateral position of the subject.

Method of Estimating of Structures in the Subject

One of the uses of the system 20 described above is to monitor the growth of tumors or other lesions in test subjects. The camera 130 attached to the endoscope 110 may provide digital images of the tumors and the two dimensional area of the tumor in the image may be estimated to monitor the growth. To estimate the dimensions of the tumor in the digital images, the system provides a mechanism for determining the scale of the tumor, as discussed further below. In reference to FIG. 2, the following discussion describes the method of estimating a tumor designated 200 that is growing in the wall of the colon, which is designated 210.

The method for estimating the tumor size includes several steps which are briefly stated as follows. First, points are selected that represent lines 215 overlying the edges of the scaling element 140. These lines 215 are extended to a point of convergence. A centerline 217 between the converging lines 215 is then calculated. A first ellipse is calculated based on the selection of a point along the centerline and a point along one of the converging lines.

As described previously, the endoscope assembly 100 includes a scaling element 140 that projects forwardly from the front end of the endoscope 110. In the present instance, the scaling element 140 is a cylindrical rod having sufficient rigidity to advance into the patient without buckling, while having sufficient flexibility to deform laterally as the element is advanced into the subject. More specifically, in the present instance, the scaling element is a 1 mm diameter metal rod.

The scaling element is inserted through the sheath 112 until it is in the field of view of the endoscope 110 and adjacent the tumor 200, as shown in FIG. 2. The scaling element 140 is oriented substantially parallel to the endoscope. Because the diameter of the scaling element is known, the scaling element can be used to estimate the size of the tumor. Although the diameter of the scaling element is constant, the perceived diameter of the scaling element diminishes as the scaling element extends away from the endoscope. In other words, the diameter of the scaling element seems smaller at a point 2 cm away from the endoscope than the diameter of the scaling element at a point 1 cm away from the endoscope. Due to this perspective, the sides of the scaling element will converge as the scaling element extends away from the endoscope, as shown in FIG. 2.

Since the scale of the scaling element varies relative to the distance from the endoscope, the point along the scaling element that intersects with the plane of the front surface of the tumor is estimated as follows. First, the image from the endoscope 110 is captured by the camera 130 as a digital image. The digital image is a raster of pixels. The image data is displayed so that the operator can select points along the edges of the scaling element 140. Specifically, the operator selects a plurality of points along each edge of the scaling element. In the present instance, the operator selects two points along each edge of the scaling element.

Based on the points selected by the operator, software calculates and constructs lines representing the edges of the scaling element and extends the lines to convergence at a vanishing point, which is designated P4 in FIG. 2. The lines of convergence, which represent the edges of the scaling element, are designated 215. The software also calculates and constructs a centerline the runs between the two edge lines. The centerline is designated 217 in FIG. 2. The points along the centerline are equally spaced from the two edge lines 215.

Since the scaling element 140 is parallel to the endoscope 110, concentric circles on the scaling element can be represented by a series of ellipses having an eccentricity equal to 2 in the image. Therefore, an ellipse is constructed that corresponds to the size of the scaling element at the point the ellipse intersects the scaling element. A second ellipse may then be constructed adjacent the front surface of the tumor 200. Based on size of the second ellipse and the known size of the scaling element, an appropriate scale can be estimated for the tumor. The construction of the ellipse(s) is described in greater detail below.

After the lines of convergence 215 and the centerline 217 are calculated and constructed, the operator selects two points along one of the markings on the scaling element. First, the operator selects the point that the marking intersects the centerline, which is designated P1 in FIG. 2. Second, the operator selects the point that the marking intersects one of the converging lines 215. The second point is designated P2 in FIG. 2. Based on the location of points P1 and P2, and the orientation of the converging lines, the software calculates an ellipse having an eccentricity of 2 that has a major diameter ending at point P2 and extending to the second converging line, and having a minor diameter terminating at point P1 along the centerline.

If the operator is able to identify the above-referenced intersection points (P1 and P2) for a marking on the scaling element 140 that intersects the plane of the front surface of the tumor, then the major diameter of the resulting ellipse may be used to determine the scale of the image data for the tumor. However, frequently the markings on the scaling element blur together as the scaling element extends away from the endoscope 110. Therefore, the operator may have difficulty accurately identifying points P1 and P2 for a marking adjacent the front of the tumor. Accordingly, a marking closer to the end of the endoscope may be selected to create a baseline ellipse, which is then used to construct a second ellipse adjacent the front edge of the tumor, as discussed further below.

After the first ellipse is constructed, the operator selects the point along the centerline that appears to intersect with the plane of the front surface of the tumor. In FIG. 2 this point is designated P3. The second ellipse is constructed using several known data elements. For instance, the second ellipse is oriented so that the major and minor diameters are parallel to the major and minor diameters of the first ellipse. Additionally, the major and minor diameters of the second ellipse correspond to the major and minor diameters of the first ellipse. Specifically, the ratio of the major diameter of the first ellipse to the distance from P1 to P4 is equal to the ratio of the major diameter of the second ellipse to the distance from P3 to P4. Based on this data, the software calculates and constructs an ellipse having an eccentricity of two passing through the intersection point P3 and having edges that intersect the lines of convergence 215. In FIG. 2, the second ellipse has a major diameter that is designated 219.

Since the diameter of the scaling element is known, it can be used as an approximation of the major diameter 219. Specifically, the length of the major diameter can be calculated in pixels. In other words, the software can calculate the length of the major diameter 219 in pixels. Since the diameter of the scaling element is known to be 1 mm, knowing the length of the major diameter in pixels provides the scale of pixels per millimeter in length. As a result, the pixel/mm scale can be used to estimate the size of the tumor 200. Specifically, points on the edges of the tumor are identified, so that geometric features of the tumor can be calculated to estimate the tumor size. For instance, in the example illustrated in FIG. 2, the points at the widest point of the tumor are selected, resulting in a line 225 reflecting the width or major diameter of the tumor. The software can calculate the length in pixels for line 225. Similarly, a point at the top edge and a point at the bottom edge of the tumor are identified, resulting in a line 226 reflecting the height or minor diameter of the tumor. The software can calculate the length in pixels for line 226. The pixel lengths for lines 225 and 226 can be converted to millimeters using the scaling factor determined as described above. The size of the tumor can then be estimated using a formula representative of the measured characteristics (i.e. lines 225, 226) and the shape of the tumor. Although this formula may vary in different applications, in the present instance the size of the tumor is estimated based on the formula:

$$\text{Area} = (a \times b) \times \pi/4$$

where a and b are major and minor axes 225, 226 respectively.

To validate the estimation methodology, a series of measurements of tumor sizes estimated by colonoscopy according to the method described above and a series of measurements of tumor sizes estimated by MRI were compared with results measured via necropsy. The results show a close correlation, and are illustrated in the graph in FIG. 4.

As described above, the system 20 allows an operator to efficiently perform a endoscopic procedure on a small mammal with little or no assistance. In one application, the system is used to measure the growth rate of colon tumors in mice. Since the tumor size can be efficiently measured without resorting to necroscopic measurements, the test subjects can be periodically monitored to evaluate the tumor growth.

In the foregoing discussion, the methodology includes a method for performing an endoscopic procedure of an animal. One exemplary procedure is the examination of lesions, and specifically may include an estimation of the size of the lesion. Such a methodology can be incorporated into a variety of applications.

For instance, in one application, the methods and device of the invention may be used to assess the efficacy of candidate therapeutic agents. In this embodiment, the methods described above further comprise administration of at least one putative therapeutic agent to an animal having a tumor burden and employing the system 20 to assess whether administration of the agent(s) affects tumor growth or burden. In this way, effective chemotherapeutic agents which inhibit or prevent tumor cell proliferation may be identified. The endoscopic method may be repeated periodically over time to temporally assess alterations in tumor burden following administration of the candidate therapeutic agent. The method may also entail repeated administration of the candidate agent to determine appropriate dose and/or route of administration. Test agents to be assessed this way include, without limitation, any compounds suspected of inhibiting tumor growth, compounds present in a combinatorial chemical library and lead compounds that have been tentatively identified in other screens.

EXAMPLE

Examination

Colonoscopies were performed using a rigid bore endoscope with a 0-degree viewing angle and 1.5 mm outer diameter (Gradient Lens Corp., Rochester, N.Y.). The scope remained stationary while the mouse was manipulated with a positioning device 20 that allowed precise positioning of the mouse relative to the endoscope tip in all directions and orientations as described above and illustrated in FIG. 1. The positioning device 20 was formed of a calibrated XY stage (Sherline Products Inc., Vista, Calif.), a vertical translation platform with 360-degree rotation (Thorlabs Inc., Newton, N.J.), and a dual axis goniometer (OptoSigma, Inc., Santa Ana, Calif.). The endoscope assembly 100 was coupled to a QImaging Micropublisher 3.3 digital camera (QImaging Corp., Surrey, BC, Canada), chosen for the small pixel size of the sensor (3.3 mm) and thermoelectric cooling of the charge coupled device (CCD). In vivo illumination was provided by a 350 watt xenon lamp (Medit Inc., Manitoba, Canada). Animals were kept under anesthesia (2% isofluorane in oxygen) and a heat lamp for the duration of the exam (10-15 minutes). The colon was insufflated with phosphate buffered saline (PBS) through the endoscopic sheath, and the degree of the abdominal distention was monitored to prevent distress. The endoscope was inserted 3 cm into the mouse anally and gradually withdrawn over time. The location of each identified tumor was recorded based on the extent to which the endoscope was inserted using gradations on the instrument.

Size Estimation and Geometric Construction

A method for the quantitative and reproducible estimation of lesion size has been developed, which involves placing an object of known size in close proximity with the tumor and using it as a reference for estimating tumor size in the resulting images. Specifically, a flexible metal rod (the biopsy forceps supplied by the sheath manufacturer) (1 mm diameter) is placed in the biopsy channel of the endoscope sheath and inserted until it is visible in the field of view of the endoscope, adjacent to the lesion, as shown in FIG. 2. The positioning device 20 facilitates placement of the mouse colon and reference object at a precise orientation relative to the endoscope tip. Using software, a geometric construction, based on estimating the position of the cylindrical rod in the image relative to the tumor, permits quantitative estimation of tumor size. By using the endoscope assembly 100 to view the tumor from a single direction, it is possible to estimate the height, width, and cross-sectional area of the tumor.

In order to quantitatively estimate lesion size, a measurement grid is constructed on the image. The operator first chooses a set of points in the 2-dimensional image that defines the reference rod in a 3-dimensional space. (The rod is modeled as a cylindrical object in the field of view.) The edges of the cylinder are then marked manually by selecting two pixels on either side of the rod. The lines formed by these points are extended to a vanishing point (P4 in FIG. 2), and a line that runs in the center between the two edge lines is calculated by software and displayed on the image. Given that the rod is held by the sheath at approximately the same angle for each image, concentric circles on the rod are represented by ellipses of eccentricity 2 in the image. The operator next estimates the point on the center line that is in close proximity with a groove on the reference rod (P1), and then marks another point (P2) on the edge of the rod along the same groove. The point on the center line closest to point P1 is calculated by software. The ellipse representing a circle on the reference rod is defined uniquely by points P1 and P2, its eccentricity, and the fact that the minor axis of the ellipse is parallel to the center of the rod.

Lesion size can be calculated from the image by choosing a point on the rod (ellipse) that is the same distance from the scope lens as the tumor. An ellipse of eccentricity 2, representing a circle on the axis of the rod, was calculated by software and drawn on the image. The minor axis of the ellipse is fixed parallel to the center line of the rod. The points of intersection of the ellipse with the edges of the reference rod are calculated as the ratio of the distance from reference point P1 to the image vanishing point P4 (D1) with the distance from the vanishing point to that of tumor point P3 (D3), and the distance of point P2 to the vanishing point (D2). Point P5 is, therefore, a point along the rod's edge, whose distance to the vanishing point is given as: $D5=D2*(D3/D1)$. The distance across the rod (perpendicular to the center line at point P5) gives the 1 mm reference distance for calibrating the size of objects in contact with the rod at that point. The longest dimension of the tumor in the image is taken as the width 225, and the size of the tumor in the perpendicular direction is taken as the height 226. The cross-sectional area is measured by outlining the edges of the tumor manually, or by assuming that the tumor cross section is elliptical in shape and computed as area=(width×height)×p/4.

MRI

Briefly, the procedure for acquiring MRI data sets from $Apc^{+Min\text{-}FCCC}$ mice is as follows. Mice were anesthetized (2% isofluorane in oxygen) and a sealed 2 French polyurethane tube (Access Technologies, Skokie, Ill.) containing 4 mM Gd-DTPA was inserted into the colon of the mouse to serve as an identifiable marker on the resulting MRI data sets. Following an intramuscular injection (200 ml) of Gd-DTPA (Magnevist, Berlex Laboratories, Hamilton, N.J.) diluted 1:10 in 1× PBS, each mouse was placed in a vertical wide-bore magnet with a field strength of 7 Tesla and a Bruker DRX300 console and microimaging accessory.

Scout images were obtained in coronal and axial orientations and used to create a high-resolution isotropic data set with a 3-dimensional gradient echo pulse sequence (256×256×64 matrix) and a voxel length of 0.133 mm, $T_E=3.3$ msec, $T_R=0.2$ sec. Once preliminary scans were completed to optimize positioning, isofluorane was reduced to 0.5% for the duration of the scan (30 minutes) and respiration was monitored using a respiratory sensor. Lesion volume was measured with a 3-dimensional planimetry technique, using software. The sections from the 3-dimensional data set were displayed in one of three orthogonal dimensions (axial, coronal, or sagittal), and the tumor was outlined manually using a combination of views. Tumor cross-sectional area was estimated from MRI data sets by displaying a slice in the axial orientation (approximating the view of the distal colon one would get through the endoscope) through the lesion, and manually measuring the height and width of the tumor in pixels. Measurements were then converted to centimeters from the known field of view and dimensions of the data set. Tumor area was computed using the formula area=(width×height)×δ/4.

Histopathologic Evaluation

Following completion of the imaging procedures, mice were euthanized by $CO_2$ asphyxiation. The colons were excised, opened lengthwise and rinsed with PBS. Gross lesions that had been imaged by either MRI or endoscopy were identified based on their distance from the anus. The height, length and diameter of each lesion were measured using calipers, and tumors were excised and fixed in 10% neutral buffered formalin for 24 hours. Paraffin-embedded sections were stained with hematoxylin and eosin and subjected to histopathologic review. An adenoma was defined as a circumscribed neoplasm composed of tubular and/or villous structures and lined with dysplastic epithelium.

Statistical Analyses

Spearman's rank correlation was used to compare tumor measurements obtained from endoscopy or MRI with those based on the measurement of gross lesions at the time of sacrifice using calipers. Statistical significance was defined as any p-value less than 0.05.

Results

Animals

Thirty-two $Apc^{+/Min-FCCC}$ mice were examined by colonoscopy. The incidence of colonic tumors within the distal region of the colon that was accessible to the endoscope (3 cm from the anus) was 66%. Among the remaining tumor-bearing mice (n=21), 38% (3/21) had colonic tumors greater than 1.5 mm in diameter. These mice received MRI scans on the day following colonoscopy.

Colonoscopy

A total of 175 colonoscopic examinations were performed on 32 mice during the course of this study. Adenomas as small as 0.5 mm in height and 1.0 mm in diameter were readily detected by colonoscopy. Tumor-bearing animals possessed one to 5 adenomas per mouse, with the majority located 1-2.5 cm from the anus. Tumors within 0.5 cm of the anus were difficult to image. Screening exams were not performed in animals with either multiple colon adenomas in close proximity or one adenoma $^>$5 mm in diameter, since advancement of the scope past these large tumors was not possible.

Validation of Tumor Size Estimates Obtained by Colonoscopy

Figure 4:
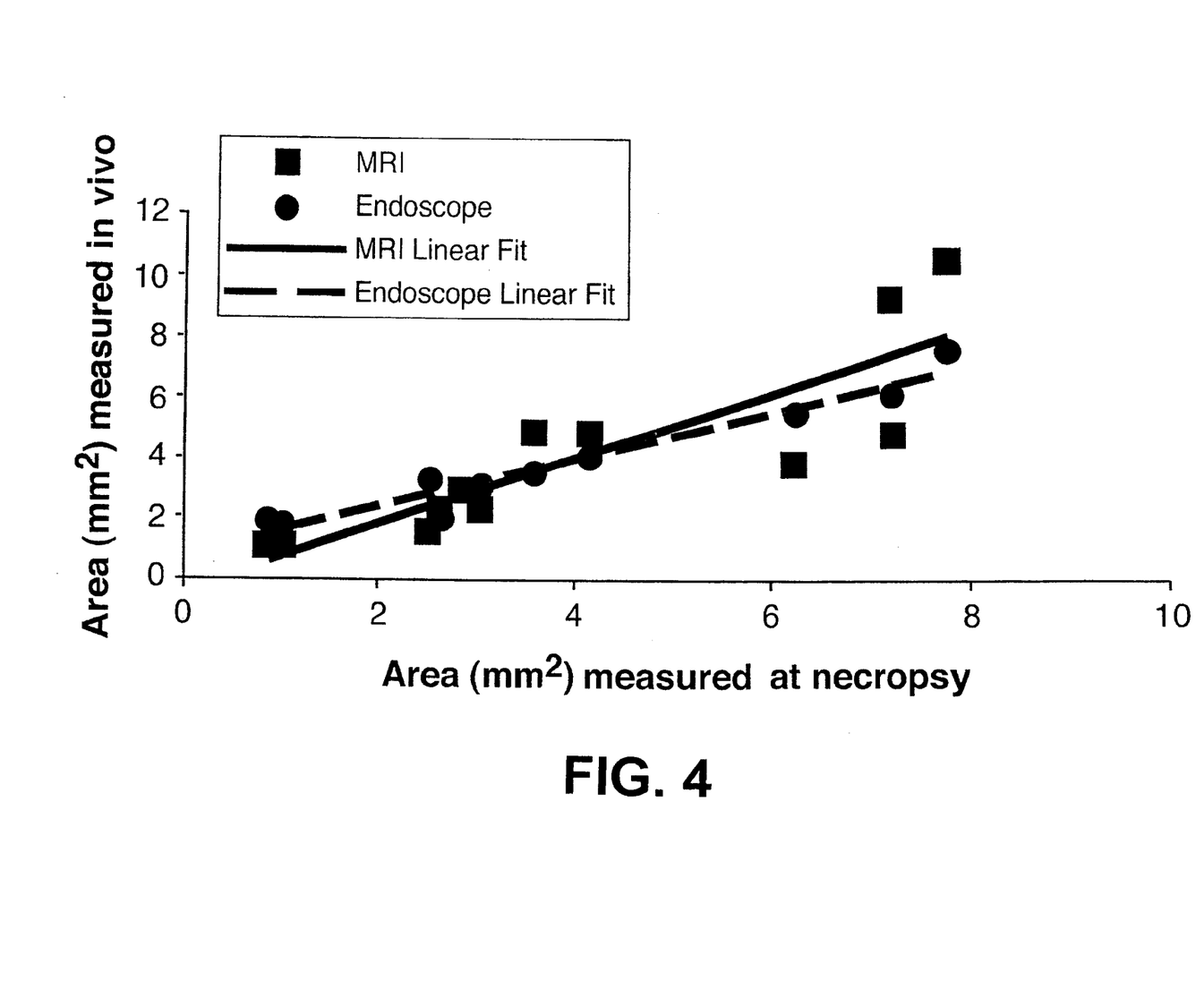
FIG. 4 is a graph of a comparison of tumor size based on results obtained by MRI and colonoscopy versus necropsy.

Lesion size estimates from colonoscopic exams were validated in a subset of animals where tumor size could be measured by colonoscopy and MRI and at necropsy (8 mice, 10 adenomas). Adenomas ranged in size from 0.8-1.7 mm in height and 2.0-2.9 mm in diameter. Size estimates (cross-sectional area as measured with the endoscope or tumor volume as determined by MRI) were compared with the same calculations based on caliper measurements at necropsy. The cross-sectional area calculated from endoscopic images was also compared with that obtained from MRI scans. A strong correlation was observed between the cross-sectional area of a lesion estimated from colonoscopic images and that based on caliper measurements at necropsy (Spearman's rank correlation r=0.92; p-value=$2.588 \times 10^{-5}$) (FIG. 4). This correlation was comparable to that achieved when lesion volume was calculated from MRI scans and compared with the estimated volume of the gross lesion at necropsy (r=0.91, p-value=$2.2 \times 10^{-16}$). A direct comparison of lesion size as determined by the MRI and colonoscopy was made by computing a cross-sectional area from axial sections of the MRI scans and correlating it with similar measurements obtained at the time of colonoscopy. Comparison of the cross-sectional area of a colon adenoma as computed from MRI scans and colonoscopic images yielded a correlation coefficient (r=0.9, p-value=$6.588 \times 10^{-5}$) that was very similar to that obtained when comparing area from the MRI scan vs. necropsy (r=0.94, p-value=$2.2 \times 10^{-16}$).

In light of the foregoing, the methods and system described herein may be adapted to a variety of applications in which a test animal is examined endoscopically to evaluate the effect, if any on the condition to be treated. In the foregoing description, a tumor lesion is identified as the area of interest, however the methodology is not limited to the examination of tumors, rather any aberrant tissue or characteristic body part may be examined using the system of the present invention.

It will be recognized by those skilled in the art that changes or modifications may be made to the above-described embodiments without departing from the broad inventive concepts of the invention. For instance, in the foregoing example, the system has been described in connection with a colonoscopy. However, the system can also be used in other procedures, such as inspection of the esophagus, trachea or bronchial spaces. Similarly, the system can be used in procedures in which a small incision is made in the subject so that the endoscope can be inserted into the subject. Further still, as described above, the scaling element is described as a generally cylindrical element that is positioned adjacent the tumor 200 with the scaling element extending past the tumor. Alternatively, the scaling element may be configured to include an engagement portion configured to engage the front surface of the tumor. The engagement portion may extend transverse the longitudinal axis of the endoscope. Since the engagement portion engages the tumor, the point of intersection between the front surface of the tumor and the scaling element is determined rather than being estimated. It should therefore be understood that this invention is not limited to the particular embodiments described herein, but is intended to include all changes and modifications that are within the scope and spirit of the invention as set forth in the claims.

What is claimed is:

1. A method for estimating tissue size from endoscopic images, comprising the steps of:
   inserting an endoscope into a subject to view a tissue sample within the subject;
   positioning a reference standard adjacent the tissue sample, wherein the reference standard has a known dimensional feature;
   acquiring an image of the tissue sample and the reference standard;
   constructing first and second construction lines along an edge of the reference standard and extending the first and second construction lines to a point of convergence at a vanishing point;
   calculating a reference element based on a feature of the reference standard, wherein the step of calculating a reference element comprises calculating a reference shape extending between the first and second construction lines;
   determining a scale for calculating the size of the tissue sample based upon the known dimensional feature and a characteristic of the reference shape; and
   calculating the size of the tumor using the determined scale and data from the image.

2. The method of claim 1 wherein the step of positioning the reference standard comprises moving the reference standard with the endoscope.

3. The method of claim 2 wherein the reference standard projects axially between the endoscope and the tumor.

4. The method of claim 2 wherein the reference standard is an elongated flexible element and the step of moving the reference standard comprises bending the reference standard as the reference standard is advanced within the subject.

5. The method of claim 1 wherein the steps of constructing first and second construction lines comprises the steps of:
   selecting a plurality of points along a first edge of the reference standard; and
   selecting a plurality of points along a second edge of the reference standard.

6. The method of claim 1 comprising the step of constructing a centerline extending midway between the first and second construction lines.

7. The method of claim 1 comprising the steps of:
positioning the subject on a support; and
adjusting the position or orientation of the support while the endoscope is in the subject to manipulate the position or orientation of the endoscope relative to the subject.

* * * * *

UNITED STATES PATENT AND TRADEMARK OFFICE
CERTIFICATE OF CORRECTION

| | |
|---|---|
| PATENT NO. | : 9,451,904 B2 |
| APPLICATION NO. | : 12/579529 |
| DATED | : September 27, 2016 |
| INVENTOR(S) | : Harvey Hensley and Margie Clapper |

It is certified that error appears in the above-identified patent and that said Letters Patent is hereby corrected as shown below:

In the Specification

Column 1, Line 13, insert the paragraph:
--This invention was made with government support under P30 CA069744 and U54 CA105088 awarded by the National Institutes of Health. The government has certain rights in the invention.--

Signed and Sealed this
Twenty-ninth Day of August, 2023

Katherine Kelly Vidal
*Director of the United States Patent and Trademark Office*